United States Patent [19]

Tucker et al.

[11] 3,951,147
[45] Apr. 20, 1976

[54] IMPLANTABLE INFUSATE PUMP

[75] Inventors: Elton M. Tucker, Medfield, Mass.; Elwood F. Kamperman, Belle Mead, N.J.; Richard W. Hatch, Jr., Norwell, Mass.; Charles Carswell, Wrentham, Mass.; Frank Prosl, Duxbury, Mass.

[73] Assignee: Metal Bellows Company, Sharon, Mass.

[22] Filed: Apr. 7, 1975

[21] Appl. No.: 565,798

[52] U.S. Cl. .......................... 128/260; 128/214 F
[51] Int. Cl.² ................................ A61M 5/00
[58] Field of Search .......... 128/260, 214 F, 172, 128/214 E; 222/386.5; 3/1; 210/90

[56] References Cited
UNITED STATES PATENTS

| | | | |
|---|---|---|---|
| 3,659,600 | 5/1072 | Merrill | 128/172 |
| 3,731,680 | 5/1973 | Wright | 128/214 E |
| 3,731,681 | 5/1973 | Blackshear | 128/260 |
| 3,896,806 | 7/1975 | Wichterle | 128/260 |

*Primary Examiner*—Aldrich F. Medberry
*Attorney, Agent, or Firm*—Cesari & McKenna

[57] ABSTRACT

A rechargeable infusate pump for implantation in the human body can be refilled periodically by injection through an inlet septum under the skin. A conduit from the pump outlet conducts fluid to an infusion site in the body. The needle penetrating the septum protrudes into an antechamber and discharges fluid and any foreign matter is trapped in the antechamber so that it cannot enter the pump chamber and possibly clog the pump outlet. This foreign material is removed by injecting a needle into the antechamber and drawing a vacuum to suck out the debris.

The pump also has a special ring-like outlet filter in the fluid stream between the pump chamber and its outlet to provide a maximum amount of filter area in a minimum amount of space and the pump outlet includes a special flow controller which is able to very accurately meter the infusate to the selected body site.

12 Claims, 9 Drawing Figures

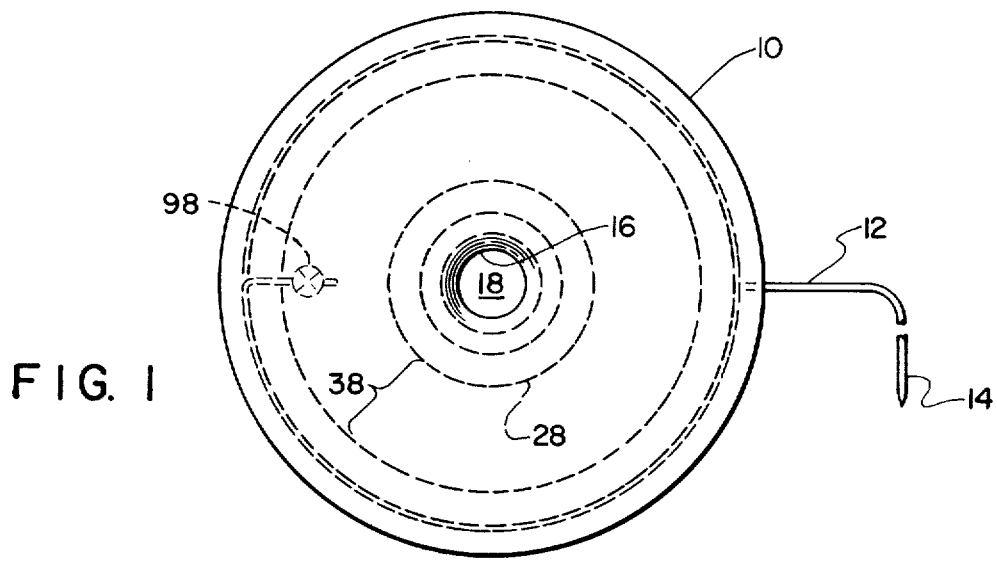
FIG. 1
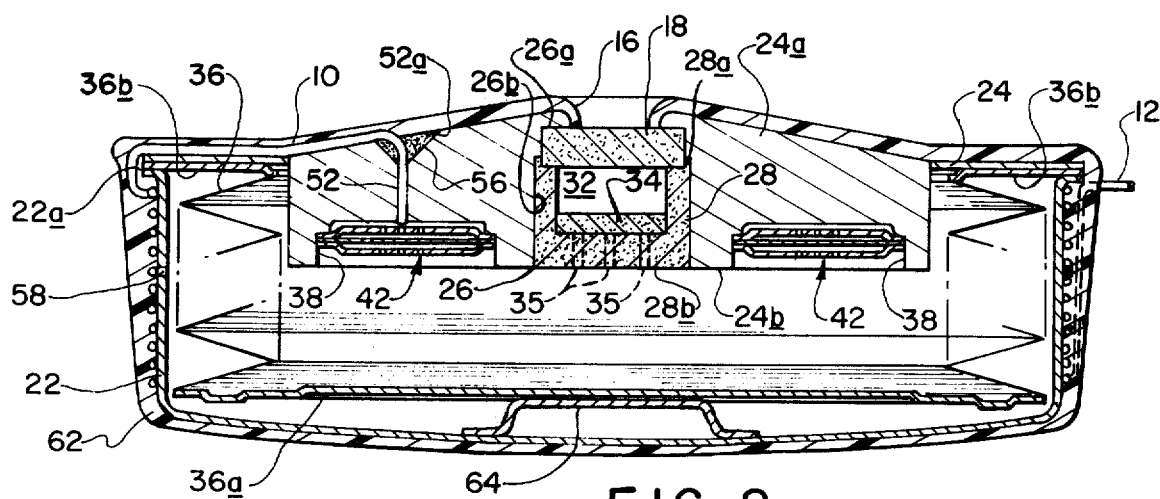
FIG. 2
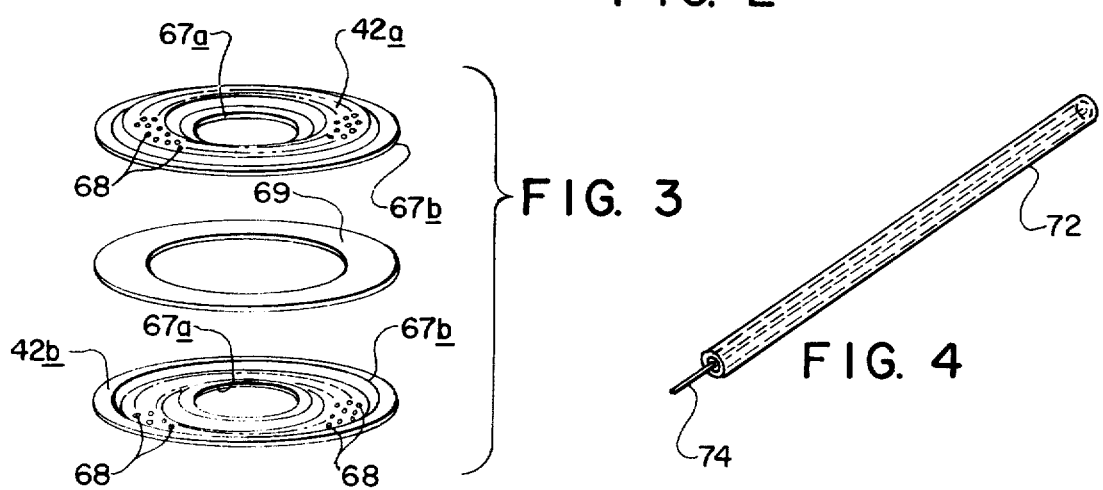
FIG. 3
FIG. 4

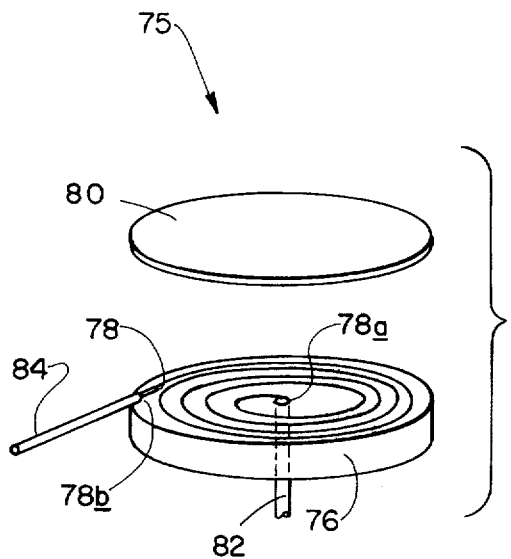
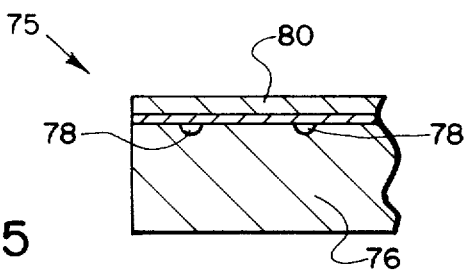
FIG. 5
FIG. 5A
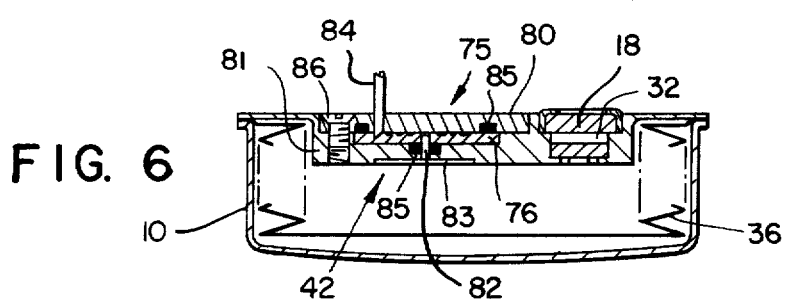
FIG. 6
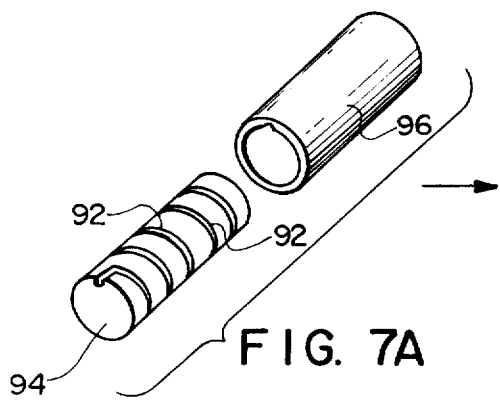
FIG. 7A
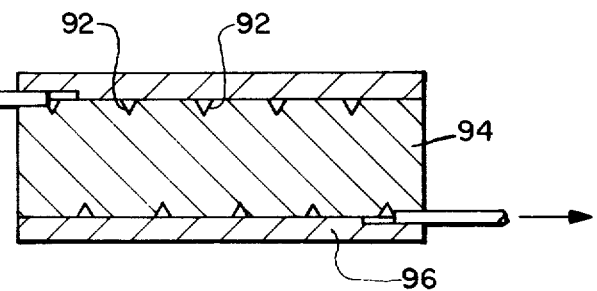
FIG. 7B

IMPLANTABLE INFUSATE PUMP

BACKGROUND OF THE INVENTION

This invention relates to an implantable infusate pump. It relates more particularly to an implantable pump having an inlet septum situated close to the patient's skin so that the pump can be refilled and recharged percutaneously.

Advances have been made in recent years in the design and development of mechanical devices for implementation in the human body. These include heart valves, heart stimulators and small external pumps for infusion of medicine to various sites in a person's body. The obvious advantage of implanting devices such as these is that there is no permanent opening through the patient's skin which could be a site of infection.

Implantable pumps were envisioned some years ago. Recently, one such pump has been developed which is particularly effective. That pump is described in U.S. Pat. No. 3,731,681, dated May 8, 1973 entitled IMPLANTABLE INFUSION PUMP. The present invention is an improvement on that pump.

One problem encountered with the prior pump is that minute amounts of hair and skin sometimes enter the pump chamber and clog the outlet tube leading to the infusion site in the body. Such obstructions slow the flow of infusate to the site and sometimes interrupt flow entirely. Apparently this foreign matter is introduced into the pump chamber when infusate is being injected through the penetrable septum to refill and recharge the pump. Such blockage could, of course, present serious problems for the patient and, at the very least, it would necessitate an operation to remove and replace the pump. Proposals to avoid this problem by placing a filter between the pump chamber and the outlet tube have not been entirely satisfactory because the debris tends to accumulate on the filter and still reduce the flow of infusate to the infusion site.

The prior implantable pump is also somewhat disadvantaged because it is not compatible enough with the human body. This is due to a variety of factors. The pump is relatively large and bulky and, therefore, requires a relatively large space in the body. Also, it contains various exterior promentories and recesses where body fluids accumulate after implantation and may become infected, resulting in a requirement for treatment or possibly pump removal. Furthermore, the pump's outlet tube does not control the flow of infusate accurately enough at the very low flow rates involved. Finally, that pump employs several turned and threaded fittings requiring gaskets, making it relatively expensive to make and prone to leakage of infusate liquid and the vapor used as a pressure source.

SUMMARY OF THE INVENTION

Accordingly, the present invention aims to provide an improved implantable pump which does not become obstructed by accumulated debris.

A further object of the invention is to provide an implantable pump which requires a minimum amount of space in the body.

Yet another object of the invention is to provide a pump of this general type which has regular, unbroken, smooth exterior surfaces to prevent infection and rejection by the body.

Another object of the invention is to provide a pump of this general type which very precisely meters very small predictable quantities of infusate to the infusion site.

Still another object of the invention is to provide an implantable pump which minimizes the chances of air bubbles being delivered to the infusion site in the body and to prevent the flow of bacteria from the pump chamber into the body.

A more specific object of the invention is to provide an implantable pump which is relatively inexpensive to make and is not prone to leakage.

Other objects will in part be obvious and will in part appear hereinafter.

The invention accordingly comprises the features of construction, combination of elements and arrangement of parts which will be exemplified in the following detailed description, and the scope of the invention will be indicated in the claims.

Briefly, the pump comprises a contoured housing having a smooth, unbroken surface giving the housing the general shape of a flat cylinder. The housing is made in two sections, to wit: a cup-like lower section having a lip and a discoid cover section whose periphery is welded to that lip.

The cover section has a relatively thick central area for accommodating the internal components of the pump. An axial passage is formed in that central portion which is counter-bored to seat a self-sealing septum or plug near the outer end of the passage. A second counter-bore slightly larger than the first accomodates a cup-shaped filter whose rim seats against the underside of the septum, thereby providing an antechamber between the plug and the filter.

A circular channel is formed in the underside of the central portion of the cover member concentric with its passage in which seats a flat washer-shaped outlet filter. Also, a welded metal bellows capsule is situated in the housing. The capsule is closed at its end facing the bottom of the lower housing section and its other end has a circular flange which is sandwiched between the welded-together peripheries of the two housing sections.

One face of the outlet filter communicates with the interior of the bellows capsule. A small passage extending from the channel in the upper housing section adjacent the opposite face of the outlet filter communicates with the pump's outlet conduit which projects through the upper housing section and conforms to the outside of the housing.

The pump is charged by flowing a volatile fluid through a fill tube into the housing outside the bellows capsule, partially filling that space, following which the fill tube is sealed by welding. This fluid should be a stable volatile liquid that exerts a vapor pressure of greater than one atmosphere at physiological temperatures (approximately 37° C) to form the vapor-liquid mixture of a chemical power source. A suitable fluid for this purpose is a fluorocarbon fluid or any one of the other fluids mentioned in the aforesaid patent. Then the entire pump is coated with a suitable material such as Silastic which is compatible with the human system.

The pump is filled initially and refilled by inserting a hypodermic needle through the self-sealing inlet septum and injecting infusate into the antechamber. The infusate filters through the inlet filter into the bellows capsule. Any material such as skin or hair is trapped in the antechamber and cannot enter the bellows capsule where it might accumulate in the bellows or clog the outlet filter or the outlet tube. The pressure generated by this injection is sufficient to extend the bellows capsule and impart a pressure to the fluorocarbon inside the housing, causing its volatile vapor phase to condense.

In use, the pump is placed in the body with the penetrable inlet septum just under the skin. The outlet tube which terminates in a catheter is then positioned at the infusion site. The patient's body temperature causes the fluorocarbon in the pump to vaporize, thereby exerting a positive pressure on the bellows capsule to force infusate through the outlet tube to the infusion site.

The outlet tube includes a flow regulator which very accurately meters the infusate to the site, even at extremely small flow rates. The flow controller will be described in more detail later.

When the pump is nearly empty, it is refilled by injecting more infusate through the inlet septum into the pump antechamber. Any accumulation of foreign material can be removed from the antechamber periodically by inserting a hypodermic needle through the septum and drawing a vacuum to suck the debris from the antechamber. This minimizes the chances of foreign matter clogging the inlet filter or finding its way into the bellows capsule.

The fact that the present pump can be refilled and recharged as well as be cleaned while remaining implanted in the patient's body minimizes patient discomfort and danger of infection. Also, since the pump very accurately meters the outflow of infusate, a predetermined dosage is delivered to the patient over a long period of time. Finally, since the entire pump is quite small and correctly configured to suit the body, it can remain in the patient's body comfortably for a long period of time.

BRIEF DESCRIPTION OF THE DRAWINGS

For a fuller understanding of the nature and objects of the invention, reference should be had to the following detailed description taken in connection with the accompanying drawings, in which:

FIG. 1 is a top plan view of an implantable pump embodying my invention;

FIG. 2 is a view of the pump in medial section on a larger scale;

FIG. 3 is an exploded perspective view showing the pump outlet filter in greater detail;

FIG. 4 is a perspective view in section on a greatly enlarged scale showing a modified flow controller used in the FIG. 1 pump;

FIG. 5 is an exploded perspective view illustrating another flow controller embodiment;

FIG. 5A is a fragmentary view in section of the FIG. 5 controller;

FIG. 6 is a sectional view on a smaller scale showing the placement of the FIG. 5 controller inside the pump housing; and FIGS. 7A and 7B illustrate still another flow controller embodiment for use in the subject pump.

DESCRIPTION OF THE PREFERRED EMBODIMENTS

Turning now to FIGS. 1 and 2 of the drawings, the pump includes a contoured housing 10 which is typically on the order of three inches in diameter and three-quarter inch thick made of titanium. The pump is implanted in the patient's body and includes a pressure power source which responds to physiological temperature to pump infusate from housing 10 through a capillary tube 12 to a catheter 14 located at an infusion site in the patient's body.

An opening 16 in one face of the housing exposes a self-sealing septum 18 and the pump is positioned in the patient's body so that septum 18 is positioned directly underneath the skin. When the pump's supply of infusate is exhausted, additional infusate is injected through the patient's skin and septum 18 into the pump. This both refills the pump and recharges its pressure power source.

Turning now to FIGS. 1 and 2, housing 10 is comprised of a cup-like lower section 22 whose rim is flared to form a lip 22a. The housing also includes a discoid upper housing section or cover 24 whose diameter equals that of lip 22a so that it forms a coextensive cover on the housing section 22.

The upper housing section or cover 24 has a relatively thick central portion 24a which supports the major components of the pump. The opening 16 in the top face of the housing is actually one end of a passage 26 that extends axially through section 24a.

Passage 26 has a counterbore 26a in which the septum 18 seats. This septum is a flexible, resilient, cylindrical plug made of a suitable material such as rubber which seals itself when punctured. A second counterbore 26b in passage 26 accommodates a cup-shaped inlet filter 28. The rim 28a of filter 28 butts against the edge margin of septum 18 while the filter bottom wall 28b is flush with the inner surface 24b of cover portion 24a.

The septum 18 and filter 28 together define an antechamber 32 inside cover portion 24a. Access to the antechamber from without is gained by inserting a hypodermic needle into the antechamber through septum 18. A relatively soft but impervious disk made of pressed polytetrolfluoroethylene or the like is desirably positioned at the bottom of filter 28 to function as a protective compliant needle stop.

The filter 28 is suitably constructed to allow the fluid injected into antechamber 32 to pass into housing 10 through small pores or passages which will exclude foreign matter such as skin, hair, dust particles, etc. A suitable filter material is porous stainless steel, for example. Alternatively, the filter 28 may be a stainless steel cup having a plurality of small passages extending through its bottom wall 28b as shown in dotted lines at 35 in FIG. 2.

Still referring to FIGS. 1 and 2, a welded titanium bellows capsule 36 is positioned inside housing 10. The capsule end 36a facing the bottom of housing section 22 is closed, while the other end of the capsule terminates in a radial flange 36b whose diameter is the same as that of housing section 24. The capsule is positioned in the housing before the housing section 24 is in place so that the flange 36b rests on lip 22a. Thereupon, the housing section 24 is seated on the flange and the peripheries of the flange and the two housing sections are all welded or otherwise bonded together to make a fluid-tight joint or seam all around the housing.

The inside surface 24b of cover portion 24a is formed with a relatively wide, shallow circular channel 38. This channel accommodates a flat washer-like outlet filter 42 shown generally at 42 which has a substantial filter surface area.

A passage 52 is formed in cover portion 24a parallel to passage 26 so that its inner end communicates with channel 38. The outer end of passage 52 is countersunk at 52a and one end of capillary tube 12 is inserted into the passage 52 and secured there by welding or a suitable bonding compound 56 which fills the space between the tube and the flared wall of the passage.

Capillary tube 12 is laid down against the top of housing section 24, turned down under lip 22a and wound around the outside of housing section 22 in the form of a coil. With this arrangement, the pump can have a long enough capillary tube to achieve the necessary flow restriction without making the overall pump package unduly bulky. After a sufficient length of tube has been coiled around the housing, the free end of the tube is bent up against the outside of the tubing coils and then outward adjacent the lip 22 as shown in FIG. 2.

The space between the bellows capsule 36 and the housing 10 is partially filled with a fluorocarbon fluid or other suitable volatile fluid by way of a fill tube 58 on the side of housing section 22 after which the fill tube is sealed by welding it closed. Finally, the entire housing 10, including the coil of capillary tube 12, is coated with Silastic or other such relatively inert material which is compatible with the human system. Of course, this coating is not applied to the exposed area of septum 18.

Before its implementation in a patient, the pump is sterilized in an autoclave. To enable the pump to withstand the pressure of the fluorocarbon which vaporizes at autoclave temperatures, the housing 10 is designed as a pressure vessel. Accordingly, the bottom wall of housing section 22 is outwardly convex in the usual manner of a pressure vessel. Also, a pedestal 64 projects up from that bottom wall to prevent the bellows capsule from being over-extended and thereby overstressed during the fill operation. Further, the amount of fluorocarbon in the pressure chamber is limited to cause all the liquid to become vapor at 140° F. At temperatures above the 140° F then, the pressure increase follows vapor thermodynamic laws other than vapor pressure laws, thereby reducing the ultimate chamber pressure by an order of magnitude.

The pump is filled and its power cell charged by injecting infusate from a hypodermic needle through septum 18 into the bellows capsule 36. The incoming fluid extends the bellows which thereupon applies pressure to the fluorocarbon in the space between the bellows capsule and the housing, causing its vapor phase to condense. If the pump is now subjected to physiological temperatures as it would be if implanted in the human body, the fluorocarbon in the pump vaporizes and the increased pressure applies a compressive load to the bellows capsule 36. This forces infusate from the capsule through tube 12 and catheter 14 to the infusion site.

When the pump is being refilled and recharged by injecting additional infusate through septum 18, any debris such as skin, hair, dirt, etc. cannot pass through filter 28 into the bellows capsule and is thus trapped in antechamber 32. Consequently, there is no likelihood of the outlet filter 42, which is provided primarily to prevent transmission of air bubbles through tube 12, becoming clogged. Chances of this are even less likely because of the makeup of filter 42.

As best seen in FIGS. 2 and 3, filter 42 comprises a pair of identical slightly dished sections 42a and 42b, both having inner and outer flanged edges 67a and 67b. A multiplicity of small openings 68 are provided all around sections 42a and 42b. A flat washer-shaped high efficiency filter 69 is seated between the two sections following which their flanged edges 67a and 67b are welded together. Thus, the outlet filter 42 has a very large effective area, e.g., on the order of 1½ square inches. Consequently, blockage of even a relatively large portion of its surface would not at all affect the flow rate of infusate to the infusion site because the required flow rates are so low. Needless to say, with the double protection afforded by the inlet and outlet filters 28 and 42, there is virtually no chance of the outlet tube 12 or catheter 14 becoming clogged by foreign matter.

Any accumulation of debris in antechamber 32 can be swept out from time to time by injecting a hypodermic needle through the septum 18 into the antechamber and drawing a vacuum on the needle so that all such debris is sucked out through the needle. Consequently, there is little chance of the inlet filter 28 becoming clogged and thereby interfering with the filling and recharging of the pump. Since all of these questions, namely, refilling, recharging, and cleaning, can be performed while the pump remains inside the patient, there is minimal danger of infection and minimum discomfort to the patient. Also, as seen from the drawing figures, the pump is a hermetically sealed device with no threaded fittings or gaskets that might tend to leak. Further, it is specially contoured with no promontories or crannies and occupies a minimum amount of space. Therefore, it should be able to remain in the patient for a long period of time.

The long length of capillary tube 12 coiled around housing 10 and leading to the patient's infusion site functions as a flow controller which very accurately meters the infusate to the body site as described in the aforesaid patent. FIG. 4 illustrates another controller embodiment which is able to meet the very small flow requirements with even greater accuracy and yet permit use of a much shorter length of capillary tube 12 than is needed in the FIG. 1 controller. This controller is also much easier to produce since larger diameters can be used.

In practice, it is extremely difficult, if not impossible, to make very small diameter capillary tubing and still maintain the accuracy of the bore diameter along the entire length of the tubing. By very small, we mean tubing having a bore on the order of 0.07 millimeter in inside diameter. As the bore diameter decreases, it becomes increasingly difficult to make satisfactory tubing.

The flow controller illustrated in FIG. 4 employs a length of capillary tube 72 having a relatively large bore diameter on the order of 0.5 millimeter. Such tubing is relatively easy to make to an accuracy of ± 0.005 millimeter.

Placed inside tube 72 is a wire 74 whose diameter is smaller than the inside diameter of tube 72. With today's technology, it is relatively easy to draw a very small wire filament having an extremely consistent diameter along its entire length, e.g. ± 0.002 millimeter. In other words, it is much easier to control the diameter of a wire than the inside diameter of a tube when very small diameters are involved. Accordingly, by properly selecting the wire 74 diameter and length, the fluid metering properties of the flow controller can be selected extremely accurately. Of course, more than one wire 74 may be placed in tube 72 to achieve the desired flow control.

FIGS. 5 and 5A illustrate another flow controller embodiment shown generally at 75 which also achieves very accurate control over the flow of infusate. It comprises a disk 76 having a spiral groove 78 inscribed in its top face. The scribing can be accomplished with extreme accuracy so that the cross section of the groove can be selected and maintained substantially constant throughout the entire length of the groove. The spiral groove extends from a point 78a at the center of the disk to a point 78b at its rim. Then a plate 80 is placed flush against the scribed face of the disk and bonded thereto, thereby forming a spiral tunnel extending from the center of the sandwich to its edge. This flow controller embodiment can be placed inside the pump as shown in FIG. 6, with disk 80 forming part of the pump cover 81. Point 78a is placed to communicate via a conduit 82 directly with the outlet side of an outlet filter 83 mounted in the underside of the pump cover. Gaskets 85 are provided to prevent leakage between the disk, plate and cover and a screw 86 holds the plate in place on the cover 81. From the outlet tube 84 which is attached by welding or suitable epoxy bonding to point 78b in filter 42, the infusate is delivered to the body site via a suitable Silastic catheter.

It is also obvious that a spiral groove 92 can be formed on the outside of a cylinder 94 and the cylinder pressed into a close fitting tube 96 as shown in FIGS. 7A and 7B to achieve the same type of performance. This controller would be situated inside the pump housing in much the same manner as the controller 75 illustrated in FIG. 6.

Since the scribing of the groove in the disk 76 or cylinder 94 can be performed with extreme accuracy, the cross section of the resulting tunnel is also very accurate and, hence, its flow control characteristics can be set precisely. Of course, it is also feasible to have two or more tunnels connected in parallel to obtain the desired fluid flow or to select between tunnels to achieve the desired flow.

It should be appreciated that the subject pump may serve more than one flow controller of the types shown in FIGS. 1, 4, 5 and 7. This simply involves adding more tube openings in the pump header. The added outlets may be for purposes of redundancy or for functional control.

Also, the outlet tube from the pump can be provided with a shutoff valve as indicated in dotted lines at 98 in in FIG. 1 so that administration of the fluid can be controlled by physician or patient. Preferably, this valve would be mounted in the top wall of the pump adjacent the patient's skin and be opened (or closed if normally open) by external pressure, magnetic force or other such energy that can be transmitted through the patient's skin without harm to the patient.

Thus, the pump described herein should be an effective device for metering various types of fluids to selected sites in the human body over a long term and it will be seen that the objects set forth above, among those made apparent from the preceding description, are efficiently attained. Further, since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

We claim:

1. An implantable infusate pump of the type having an infusate chamber, an inlet to the chamber, a self-sealing septum closing the inlet, an outlet from the chamber, and a power cell for forcing infusate from the chamber through the outlet, the improvement comprising an antechamber in the fluid stream between the pump inlet and the chamber and filter means in the fluid path between the antechamber and the chamber so that when the pump is refilled via its inlet by injecting infusate fluid through the septum, any foreign matter entrained in the incoming fluid is trapped in the antechamber and cannot enter the chamber and possibly clog its outlet.

2. The pump defined in claim 1 wherein the filter means is a cup-shaped member with its open end positioned directly opposite the septum so that the member and septum between them form the antechamber.

3. The pump defined in claim 2 wherein the cup-shaped member is made of porous stainless steel or titanium.

4. The pump defined in claim 2 wherein the cup-shaped member has an array of very small passages extending through its bottom wall and communicating with the chamber.

5. The pump defined in claim 1 and further including one or more flow controllers connected to the pump outlet for metering small quantities of infusate to an infusion site.

6. The pump defined in claim 5 wherein the flow controller comprises a length of capillary tubing connected to the pump outlet and one or more small diameter wires extending through the capillary tubing, the number, length and diameter of said wires being selected to obtain a determined flow of infusate from the pump.

7. The pump defined in claim 5 wherein the flow controller comprises a first body defining a groove extending along a surface of the body from a first location to a second location thereon. A second body having a surface coextensive with the first body surface, means for securing the two bodies together face-to-face so that the second body surface covers the groove in the first body surface to form a tunnel extending from the first location to the second location, means for connecting one end of the tunnel to the pump outlet and a length of capillary tubing connected at one end to the other end of the tunnel.

8. The pump defined in claim 7 wherein the first and second bodies are flat plates with opposing faces and the groove extends along the face of the first body.

9. The pump defined in claim 7 wherein the first body is a cylinder, the groove spirals around the curved wall of the cylinder and the second body is a tube which snugly receives the cylinder.

10. The pump defined in claim 5 and further including a shutoff valve in the fluid path at the outlet side of the chamber, said valve being positioned on the pump adjacent to the septum and being actuatable after implantation of the pump by external means.

11. The pump defined in claim 1 wherein the chamber comprises a welded metal bellows.

12. The method of cleaning debris from an implantable infusion pump of the type having an inlet including a self-sealing septum and an infusate chamber, the improvement comprising the steps of forming an antechamber between the septum and the infusate chamber, placing a filter in the fluid path between the antechamber and the chamber to trap foreign material present due to percutaneous injection of infusate intto the antechamber when refilling the pump and removing debris from the antechamber by injecting a needle through the septum into the antechamber and drawing a vacuum in the needle to suck the debris from the antechamber.

* * * * *